United States Patent [19]

Behre et al.

[11] 4,180,521
[45] Dec. 25, 1979

[54] PROCESS FOR THE PREPARATION OF NAPHTHALENE-1,3,6-TRISULPHONIC ACID

[75] Inventors: Horst Behre, Odenthal; Rolf Pütter, Duesseldorf; Guido Steffan, Odenthal, all of Fed. Rep. of Germany

[73] Assignee: Bayer Aktiengesellschaft, Leverkusen, Fed. Rep. of Germany

[21] Appl. No.: 886,696

[22] Filed: Mar. 15, 1978

[30] Foreign Application Priority Data

Apr. 9, 1977 [DE] Fed. Rep. of Germany ....... 2716029

[51] Int. Cl.$^2$ .......................................... C07C 143/30
[52] U.S. Cl. ................................................. 260/505 C
[58] Field of Search ..................................... 260/505 C

[56] References Cited

U.S. PATENT DOCUMENTS 1,311,090  7/1919  Pratt et al. ...................... 260/505 C

FOREIGN PATENT DOCUMENTS 27-4575  11/1952  Japan .

Primary Examiner—Joseph E. Evans
Attorney, Agent, or Firm—Sprung, Felfe, Horn, Lynch & Kramer

[57] ABSTRACT

A process has been invented for the preparation of naphthalene-1,3,6-trisulphonic acid by sulphonating naphthalene with sulphuric acid and oleum, characterized in that naphthalene and most of the oleum are simultaneously metered into sulphuric acid or oleum of low concentration, which has been initially introduced, at about 140° to 240° C., the temperature is kept at about 140° to 240° C. for some time, the remainder of the oleum is then added at about 140° to 240° C. and the mixture is then further stirred for some time.

Naphthalene-1,3,6-trisulphonic acid is a known important intermediate used, for example, in the preparation of T-acid, H-acid and chromotropic acid.

11 Claims, No Drawings

PROCESS FOR THE PREPARATION OF NAPHTHALENE-1,3,6-TRISULPHONIC ACID

The present invention relates to a process for the preparation of naphthalene-1,3,6-trisulphonic acid by the sulphonation of naphthalene.

Naphthalene-1,3,6-trisulphonic acid is an important intermediate product for the preparation of dyestuff intermediate products, for example T-acid, H-acid and chromotropic acid, and a stabiliser for diazo compounds (see Ullmanns Enzyklopädie der technischen Chemie (Ullmann's Encyclopaedia of Industrial Chemistry), 3rd edition, volume 12, page 596 to 597). It is known (FIAT Final Report No. 1,016, page 37) to prepare naphthalene-1,3,6-trisulphonic acid as follows: naphthalene is introduced into sulphuric acid monohydrate (=100% strength sulphuric acid) at 20° C. and the reaction mixture is warmed to 80° to 85° C. and kept at this temperature for one hour. The mixture is then heated to 145° C. and, after cooling to 85° C., is diluted with further sulphuric acid monohydrate, and most of an amount of 65% strength oleum is added at 40° C. in the course of 8 hours. The reaction mixture is heated to 145° C., kept at this temperature for 2.5 hours and cooled down to 60° C., further 65% strength oleum is added and the mixture is heated to 150° to 155° C. for 2 to 3 hours. Naphthalene-1,3,6-trisulphonic acid is not isolated from the reaction mixture, but the entire mixture is used for the further processing to give T-acid.

A process for the isolation of naphthalene-1,3,6-trisulphonic acid, in which naphthalene is sulphonated with sulphuric acid and fuming sulphuric acid, seed crystals or water and optionally seed crystals are added to the reaction mixture, which in theory contains at least 98% of sulphuric acid, and the sulphuric acid concentration is adjusted to between 80 and 98% strength, is known from Japanese Offenlegungsschrift (Japanese Published Specification) No. 96,552 (1975). Naphthalene-1,3,6-trisulphonic acid thereby crystallises out. In this procedure, the trisulphonation of naphthalene is carried out in a similar manner to that described above, by adding naphthalene to concentrated sulphuric acid, stirring the mixture at 80° C. for one hour and at 145° C. for one hour and then cooling it, adding further concentrated sulphuric acid, subsequently cooling the mixture to 40° C., then adding 60% strength fuming sulphuric acid and stirring the mixture at 145° C. for 3 hours, and finally adding 60% strength fuming sulphuric acid again at this temperature.

These two processes are based on stepwise sulphonation of naphthalene and require long sulphonating times because of the relatively complicated temperature programme, and are therefore not very suitable for a continuous procedure.

A process for the preparation of 1-naphthylamine-3,6,8-trisulphonic acid, in which the trisulphonation of naphthalene is effected by allowing concentrated sulphuric acid or pure sulphuric acid and fuming sulphuric acid to act simultaneously on naphthalene, is known from Japanese Auslegeschrift (Japanese Published Specification) 4,575 (1952). For example, 90 to 100% strength sulphuric acid is first heated to 150° to 280° C., naphthalene and fuming sulphuric acid containing over 10% of sulphuric acid anhydride are then added simultaneously and these constituents are allowed to react at 150° to 280° C., whilst stirring.

An increased oxidative decomposition of the naphthalene, as has been shown by subsequent investigation (see Examples 4, 5 and 6) takes place in this process. In addition, the sulphonation mixture contains considerable amounts of naphthalene-1,3,5,7-tetrasulphonic acid. A higher consumption of sulphuric acid monohydrate and oleum is required compared with other known processes. A further disadvantage is the increased corrosion at the high reaction temperatures. In general, the high yields of naphthalene-1,3,6-trisulphonic acid indicated are not achieved. This process is therefore uneconomic and industrially is not more advantageous than other known processes. Obviously, it has therefore hitherto not been used industrially.

A process has now been found for the preparation of naphthalene-1,3,6-trisulphonic acid by sulphonating naphthalene with sulphuric acid and oleum, which is characterised in that naphthalene and most of the oleum are simultaneously metered into sulphuric acid or oleum of low concentration, which has been initially introduced, at about 140° to 240° C., the temperature is kept at about 140° to 240° C. for some time, and then the remainder of the oleum is added at about 140° to 240° C. and the mixture is then further stirred for some time.

The formation of naphthalene-1,3,5,7-tetrasulphonic acid is largely avoided in the process according to the invention. Furthermore, naphthalene-1,3,6-trisulphonic acid is obtained in high yield and with a shortened reaction time.

The process according to the invention can be carried out, for example, by allowing naphthalene and most of the oleum to run simultaneously into sulphuric acid, which has been initially introduced, at about 140° to 240° C., preferably at about 150° to 190° C. and particularly preferably at about 160° to 180° C., in the course of about 10 to 200 minutes, preferably in the course of about 30 to 90 minutes (=simultaneous metering). In this procedure, the naphthalene can be metered in the solid form or in the molten state. Suitable sulphuric acid concentrations are about 80 to 100% by weight. Oleum containing up to about 20% by weight of sulphur trioxide can also be used in the initial material. Sulphuric acid monohydrate (=100% strenght sulphuric acid) is preferably employed.

The sulphur trioxide content in the oleum running in can be, for example, about 10 to 100% by weight, preferably about 50 to 80% by weight. In particular, commercially available, approximately 65% strength oleum can be employed.

About 1 to 10 mols, preferably about 2 to 4 mols, of about 80% strength sulphuric acid to about 20% strength oleum, for example, can be initially introduced per mol of naphthalene. About 1.8 to 3 mols, preferably about 2.4 to 2.8 mols, of sulphur trioxide in the form of oleum can then be allowed to run in per mol of naphthalene during the simultaneous metering.

A particularly favorable embodiment of the process according to the invention consists of carrying out the simultaneous metering with a slight first running of naphthalen, for example, of about 5 to 10% of the total naphthalene to be introduced. Local excesses of sulphur trioxide and the formation of naphthalene-1,3,5,7-tetrasulphonic acid can thus be largely avoided.

After the simultaneous metering has ended, the reaction mixture is kept, for example, at about 140° to 240° C. for about 0.25 to 10 hours, preferably at about 160° to 180° C. for about 1 to 4 hours. Further oleum is then added and the trisulphonation is brought to completion at about 140° to 240° C. in the course of about 0.25 to 4 hours, preferably at about 160° to 180° C. in the course of about 0.5 to 2.5 hours. It is possible here to employ, for example, about 0.01 to 2 mols, preferably about 0.2 to 0.7 mol, of sulphur trioxide in the form of oleum per mol of naphthalene.

The initial introduction of sulphuric acid, the simultaneous metering of naphthalene and oleum and the addition of the remainder of the oleum are preferably carried out at the same temperature within the ranges indicated.

The addition of the oleum in two parts is an essential characteristic of the process according to the invention, most of the oleum, for example about 1.8 to 3.0 mols of sulphur trioxide in the form of oleum, per mol of naphthalene employed, being added together with naphthalene and the remainder of the oleum, for example about 0.01 to 2.0 mols of sulphur trioxide in the form of oleum, per mol of naphthalene employed, being added after, for example, about 0.25 to 10 hours.

Compared with the processes carried out industrially, the process according to the invention has a number of advantages. Thus, because heating and cooling times are omitted, the reaction time is substantially shorter. The thermomechanical load on the sulphonating kettle or kettles is less since it is possible to carry out the process at a virtually constant temperature. The energy requirement is also less since heating and cooling several times is avoided. Finally, the process according to the invention is suitable for a continuous procedure. The yield and purity of the naphthalene-1,3,6-trisulphonic acid prepared by the process according to the invention are substantially better than in the process of Japanese Auslegeschrift (Japanese Published Specification) 4,575 (1952), and are about the same or only slightly poorer compared with those of the process according to FIAT Final Report No. 1,016, page 37 or of Japanese Offenlegungsschrift (Japanese Published Specification) No. 96,552 (1975), whilst achieving the abovementioned advantages.

It is surprising that the process according to the invention leads to such good results, since at the relatively high temperatures exclusively used and the simultaneous addition of naphthalene and oleum, side reactions and decomposition would be expected to a relatively great extent. The product present after carrying out the process according to the invention can be further used in any desired manner without isolating the naphthalene-1,3,6-trisulphonic acid. For example, it is suitable for the preparation of T-acid and H-acid, it being possible to carry out the steps of nitration, adding chalk, reduction and separating out of the T-acid and conversion of the T-acid into H-acid according to FIAT Final Report No. 1,016, page 32 to 39, or in another manner.

EXAMPLES

EXAMPLE 1

294 g (3.0 mols) of sulphuric acid monohydrate (=100% strength sulphuric acid) are initially introduced, at 160° C., into a sulphonating apparatus consisting of a 2 liter six-necked flask, or a sulphonating beaker, with a sabre-shaped stirrer, a reflux condenser, a thermometer, a gas inlet tube for nitrogen and two dropping funnels, one of which, for naphthalene, can be heated. After flushing the apparatus with nitrogen, 128 g (1.0 mol) of liquid naphthalene and 308 g of 65% strength oleum (2.5 mols of free $SO_3$) are allowed to run in simultaneously at 170° C. in the course of 30 minutes so that a small amount of naphthalene runs in first. The reaction mixture is kept at 170° C. for 120 minutes (1st stirring time), 65 g of 65% strength oleum (0.53 mol of free $SO_3$) are added at the same temperature in the course of 10 minutes and the mixture is stirred for a further 75 minutes at 170° C. (2nd stirring time). The resulting naphthalene-trisulphonic acid isomer mixture is further processed, without intermediate isolation of the naphthalene-1,3,6-trisulphonic acid, by nitration, adding chalk and reduction with iron by Bechamp's method to give a naphthylamine-trisulphonic acid isomer mixture (T-acid isomer mixture).

The yield of naphthalene-1,3,6-trisulphonic acid is 72%, relative to naphthalene, or 73.5%, relative to the sum of naphthalene-trisulphonic acids. The yield of 1-naphthylamine-3,6,8-trisulphonic acid (T-acid) is determined as 63 to 64%, relative to naphthalene, by means of high pressure liquid chromatography.

The compounds which follow were determined, by high pressure liquid chromatography, in the reaction mixture present after the sulphonation:

| | |
|---|---|
| Naphthalene-1,3,5-trisulphonic acid: | 2.4% by weight |
| Naphthalene-1,3,6-trisulphonic acid: | 33.3% by weight |
| Naphthalene-1,3,5,7-tetrasulphonic acid: | 0.6% by weight |
| Dinaphthylsulphone-tetrasulphonic acid: | about 2% by weight |
| Sulphuric acid | about 53% by weight |

EXAMPLES 2a TO 2z

The procedure followed was as in Example 1, but the following reaction parameters were varied:
1. Molar ratio of naphthalene to sulphuric acid monohydrate
2. Molar ratio of naphthalene to free $SO_3$ (1st part)
3. Molar ratio of naphthalene to free $SO_3$ (2nd part)
4. Temperature
5. Metering time
6. 1st stirring time
7. 2nd stirring time The results are summarised in Table 1.

Table 1

| | Material employed Molar ratios | | | Reaction conditions | | | | Yield | | Composition of the sulphonation mixture+ | | | | |
|---|---|---|---|---|---|---|---|---|---|---|---|---|---|---|
| Example | hydrate to naphthalene | SO$_3$ to naphthalene (1st part) | Mono-SO$_3$ to naphthalene (2nd part) | Metering minutes | 1st stirring time minutes | 2nds stirring time minutes | Temperature °C. | Naphthalene 1,3,6-trisulphonic acid mol % | T-acid mol % | 1,3,5- % by weight | 1,3,6- % by weight | 1,3,7- % by weight | 1,3,5,7- % by weight | Dinaphthylsulphone-tetrasulphonic acids % by weight |
| | | | | | | | | | | naphthalene-tri -or -tetra- sulphonic acid | | | | |
| 2a | 1.2:1 | 2.8:1 | 0.2:1 | 30 | 150 | 60 | 165 | 61 | 54 | 6.1 | 36.5 | 9.7 | φ | about 2 |
| 2b | 2:1 | 2.5:1 | 0.5:1 | 30 | 240 | 60 | 160 | 66 | 59 | 4.9 | 34.8 | 9.6 | 0.3 | about 2 |
| 2c | 3:1 | 2.5:1 | 0.5:1 | 30 | 120 | 30 | 170 | 71 | 63 | 3.3 | 32.6 | 9.3 | 0.3 | about 2 |
| 2d | 4:1 | 2.6:1 | 0.4:1 | 30 | 60 | 60 | 180 | 70 | 62 | 3.0 | 29.0 | 8.2 | φ | about 2 |
| 2e | 3:1 | 2.3:1 | 0.7:1 | 30 | 180 | 120 | 165 | 62 | 55 | 2.8 | 28.7 | 9.2 | 0.2 | about 2 |
| 2f | 3:1 | 2.5:1 | 0.5:1 | 30 | 120 | 120 | 170 | 71 | 63 | 2.5 | 32.7 | 9.1 | 0.7 | about 2 |
| 2g | 3:1 | 2.6:1 | 0.4:1 | 30 | 180 | 120 | 165 | 69 | 61 | 3.1 | 31.8 | 8.5 | 0.4 | about 2 |
| 2h | 3:1 | 2.7:1 | 0.3:1 | 30 | 180 | 120 | 165 | 66 | 59 | 3.0 | 30.6 | 9.1 | 0.2 | about 2 |
| 2i | 2:1 | 2.8:1 | 0.2:1 | 30 | 240 | 120 | 160 | 67 | 60 | 4.9 | 35.6 | 8.8 | 1.2 | about 2 |
| 2k | 3:1 | 2.9:1 | 0.1:1 | 30 | 180 | 120 | 165 | 63 | 56 | 3.7 | 29.1 | 8.4 | 0.2 | about 2 |
| 2l | 2:1 | 2.6:1 | 0.4:1 | 15 | 150 | 60 | 165 | 58 | 52 | 5.7 | 30.8 | 7.2 | 2.8 | about 2 |
| 2m | 2:1 | 2.6:1 | 0.4:1 | 60 | 150 | 60 | 165 | 60 | 53 | 5.1 | 31.9 | 7.8 | 1.2 | about 2 |
| 2n | 2:1 | 2.5:1 | 0.5:1 | 30 | 120 | 60 | 160 | 68 | 61 | 5.0 | 35.8 | 9.5 | 0.2 | about 2 |
| 2o | 2:1 | 2.5:1 | 0.5:1 | 30 | 240 | 60 | 160 | 67 | 60 | 4.9 | 35.3 | 9.6 | 0.3 | about 2 |
| 2p | 1.5:1 | 2.7:1 | 0.3:1 | 30 | 180 | 60 | 165 | 60 | 53 | 5.9 | 34.3 | 9.3 | 0.4 | about 2 |
| 2q | 3:1 | 2.7:1 | 0.3:1 | 30 | 270 | 60 | 165 | 65 | 58 | 4.1 | 30.2 | 8.9 | 0.1 | about 2 |
| 2r | 3:1 | 2.5:1 | 0.5:1 | 60 | 120 | 45 | 165 | 68 | 61 | 3.9 | 31.5 | 8.6 | 0.5 | about 2 |
| 2s | 3:1 | 2.5:1 | 0.5:1 | 60 | 120 | 60 | 165 | 68 | 61 | 3.7 | 31.5 | 8.4 | 0.7 | about 2 |
| 2t | 3:1 | 2.5:1 | 0.5:1 | 60 | 120 | 75 | 165 | 69 | 62 | 3.5 | 31.7 | 8.3 | 0.8 | about 2 |
| 2u | 3:1 | 2.5:1 | 0.5:1 | 30 | 120 | 60 | 155 | 57 | 51 | 9.6 | 26.5 | 6.7 | 0.4 | about 2 |
| 2v | 3:1 | 2.5:1 | 0.5:1 | 30 | 120 | 60 | 160 | 63 | 56 | 4.0 | 29.0 | 7.3 | φ | about 2 |
| 2w | 3:1 | 2.5:1 | 0.5:1 | 30 | 120 | 60 | 165 | 68 | 61 | 3.7 | 31.5 | 8.4 | 0.6 | about 2 |
| 2x | 3:1 | 2.5:1 | 0.5:1 | 30 | 120 | 60 | 170 | 70 | 62 | 2.9 | 32.4 | 9.3 | 0.2 | about 2 |
| 2y | 3:1 | 2.5:1 | 0.5:1 | 30 | 120 | 60 | 175 | 69 | 61 | 1.6 | 31.9 | 9.1 | 1.4 | about 2 |
| 2z | 3:1 | 2.5:1 | 0.5:1 | 30 | 120 | 60 | 180 | 69 | 61 | 1.2 | 31.8 | 9.9 | 1.1 | about 2 |

+ the remainder to make up 100% is virtually exclusively sulphuric acid

EXAMPLE 3

The procedure followed was as in Example 1, but a kettle having a capacity of 6 m$^3$ was used and 1,000 kg of naphthalene, a total of 2,270 kg of sulphuric acid monohydrate and a total of 2,900 kg of 65% strength oleum, which were added in two parts in the same ratio as described in Example 1, were employed. The yield of naphthalene-1,3,6-trisulphonic acid was 70 to 71%, relative to naphthalene. The yield of T-acid was 62 to 63% (relative to naphthalene).

The compounds which follow were determined, by high pressure liquid chromatography, in the reaction mixture present after the sulphonation:

| | |
|---|---|
| Naphthalene-1,3,5-trisulphonic acid | 3.3% by weight |
| Naphthalene-1,3,6-trisulphonic acid | 32.6% by weight |
| Naphthalene-1,3,7-trisulphonic acid | 9.0% by weight |
| Naphthalene-1,3,5,7-tetrasulphonic acid | 0.7% by weight |
| Dinaphthylsulphone-tetrasulphonic acids | about 2% by weight |
| Sulphuric acid | about 53% by weight |

EXAMPLE 4 (comparison example corresponding to Japanese Auslegeschrift (Japanese Published Specification) No. 4,575 (1952))

300 g (3.06 mols) of sulphuric acid monohydrate were initially introduced, at 170° C., into a sulphonating apparatus such as is described in Example 1. After flushing the apparatus with nitrogen, 128 g (1.0 mol) of liquid naphthalene and the entire amount of 373 g of 65% strength oleum (3.03 mols of free SO$_3$) were allowed to run in simultaneously at 180° C. in the course of 30 minutes and the reaction mixture was stirred for a further 2 hours at 180° C.

The yield of naphthalene-1,3,6-trisulphonic acid was 63%, relative to naphthalene. The following contents of compounds were determined in the reaction mixture:

| | |
|---|---|
| Naphthalene-1,3,5-trisulphonic acid: | 1.9% by weight |
| Naphthalene-1,3,6-trisulphonic acid: | 28.9% by weight |
| Naphthalene-1,3,7-trisulphonic acid: | 0.2% by weight |
| Naphthalene-1,3,5,7-tetrasulphonic acid: | 12.4% by weight |
| Dinaphthylsulphone-tetrasulphonic acids: | about 3% by weight |
| Sulphuric acid | about 53% by weight |

EXAMPLE 5 (comparison example corresponding to Japanese Auslegeschrift (Japanese Published Specification) No. 4,575 (1952))

The procedure followed was as in Example 4, but the reaction temperature was kept at 170° C. and stirring was continued for 4 hours. A yield of naphthalene-1,3,6-trisulphonic acid of 61%, relative to naphthalene, was obtained. The contents of the following substances were determined in the reaction mixture:

| | |
|---|---|
| Naphthalene-1,3,5-trisulphonic acid: | 10.1% by weight |
| Naphthalene-1,3,6-trisulphonic acid: | 28.0% by weight |
| Naphthalene-1,3,7-trisulphonic acid: | 6.5% by weight |
| Naphthalene-1,3,5,7-tetrasulphonic acid: | 0.7% by weight |
| Dinaphthylsulphone-tetrasulphonic acids: | about 2.5% by weight |

EXAMPLE 6 (comparison example corresponding to Japanese Auslegeschrift (Japanese Published Specification) No. 4,575 (1952))

The procedure followed was as in Example 4, but the reaction temperature was kept at 160° C. and stirring was continued for 6 hours. A yield of naphthalene-1,3,6-trisulphonic acid of 61%, relative to naphthalene, was obtained. The content of the following substances was determined in the reaction mixture:

| | |
|---|---|
| Naphthalene-1,3,5-trisulphonic acid: | 10.5% by weight |
| Naphthalene-1,3,6-trisulphonic acid: | 27.7% by weight |
| Naphthalene-1,3,7-trisulphonic acid: | 7.0% by weight |
| Naphthalene-1,3,5,7-tetrasulphonic acid: | 0.1% by weight |
| Dinaphthylsulphone-tetrasulphonic acids: | about 3.5% by weight |

What is claimed is:

1. Process for the preparation of naphthalene-1,3,6-trisulphonic acid by sulphonating naphthalene with sulphuric acid and oleum, characterized in that naphthalene and most of the oleum are simultaneously metered over a period of about 10 to 200 minutes into sulphuric acid or oleum of low concentration, which has been initially introduced, at about 140° to 240° C., all of the naphthalene being added by the end of the simultaneous metering, the temperature is kept at about 140° to 240° C. for some time, the remainder of the oleum is then added at about 140° to 240° C., the time between the end of the first addition of oleum and the beginning of the second addition of oleum being about 0.25 to 10 hours, and the mixture is then further stirred for some time.

2. Process according to claim 1, characterized in that 80 to 100% strength sulphuric acid or oleum containing up to 20% by weight of sulphur trioxide is initially introduced.

3. Process according to claim 1, characterized in that about 1 to 10 mols of 80 to 100% strength sulphuric acid are initially introduced per mol of naphthalene employed.

4. Process according to claim 1, characterized in that about 1.8 to 3 mols of sulphur trioxide in the form of oleum containing 10 to 100% by weight of sulphur trioxide, per mol of naphthalene, are allowed to run in simultaneously with naphthalene.

5. Process according to claim 1, characterized in that after adding naphthalene and most of the oleum, the temperature of about 160° to 180° C. is kept for about 1 to 4 hours.

6. Process according to claim 1, characterized in that oleum with a sulphur trioxide content of about 10 to 100% by weight, in an amount which corresponds to about 0.01 to 2.0 mols of sulphur trioxide per mol of naphthalene, is employed as the remainder of the oleum.

7. Process according to claim 1, characterized in that after adding the remainder of the oleum, the trisulphonation is brought to completion in about 0.25 to 4 hours.

8. Process according to claim 1, characterized in that the reaction is carried out at temperatures from about 160° to 180° C.

9. Process according to claim 1, characterized in that the simultaneous addition of naphthalene and oleum is carried out with a slight first running of naphthalene.

10. Process according to claim 1 wherein the simultaneous metering of oleum and naphthalene into sulfuric acid is carried out over a period of 30 to 90 minutes.

11. Process for the preparation of naphthalene-1,3,6-trisulphonic acid by sulphonating naphthalene with sulphuric acid and oleum, characterized in that naphthalene and most of the oleum are simultaneously metered over a period of about 30 to 90 minutes into sulphuric acid or oleum of low concentration, which has been initially introduced, at about 140° to 240° C., all of the naphthalene being added by the end of the simultaneous metering, the temperature is kept at about 140° to 240° C. for some time, the remainder of the oleum is then added at about 160° to 180° C., the time between the end of the first addition of oleum and the beginning of the second addition of oleum being about 0.25 to 10 hours, and the mixture is then further stirred for some time.

* * * * *